United States Patent
Philips

[11] Patent Number: 6,016,801
[45] Date of Patent: Jan. 25, 2000

[54] NITROUS OXIDE DELIVERY SYSTEM

[76] Inventor: Monir Wasef Philips, 3344 Sandy Ridge Dr., Clearwater, Fla. 34621

[21] Appl. No.: 08/922,830

[22] Filed: Sep. 3, 1997

[51] Int. Cl.[7] .................................................. A61M 15/00
[52] U.S. Cl. ............................... 128/203.12; 128/202.16; 128/202.21; 131/347
[58] Field of Search ........................ 128/200.22, 202.16, 128/203.12, 203.13, 203.14, 205.13, 205.15, 201.28, 204.26, 206.29; 131/347, 352, 369

[56] References Cited

U.S. PATENT DOCUMENTS

| | | | |
|---|---|---|---|
| D. 304,771 | 11/1989 | Katayama | D27/163 |
| D. 315,032 | 2/1991 | Hayes | D27/163 |
| D. 371,632 | 7/1996 | Truelove | D27/163 |
| D. 371,633 | 7/1996 | Chenard | D27/163 |
| 2,920,623 | 1/1960 | Holt | 128/203.12 |
| 3,200,819 | 8/1965 | Gilbert | 128/202.21 |
| 3,631,856 | 1/1972 | Taylor | 128/202.21 |
| 3,721,240 | 3/1973 | Tamburri | 128/202.21 |
| 4,549,563 | 10/1985 | Monnier | 137/100 |
| 4,685,478 | 8/1987 | Malil | 131/297 |

FOREIGN PATENT DOCUMENTS 2665639  2/1992  France ........................ 128/202.21

*Primary Examiner*—Aaron J. Lewis
*Assistant Examiner*—Teena Mitchell

[57] ABSTRACT

A first nitrous oxide delivery system (110) has a first housing (112) configured in a shape of a cigar. The first housing (112) has a first housing fill (112A) which is insulation to prevent frosting when the nitrous oxide is released from the nitrous oxide container (16). The first nitrous oxide delivery system (110) further comprises a mouthpiece (14) is positioned within the first housing front (112F). The first nitrous oxide delivery system (110) further comprises a nitrous oxide container (16) positioned within the first housing middle chamber (112MA). The nitrous oxide container (16) comprises a nitrous oxide container outlet (16A) sealaby attached to the front mouthpiece (14F). The nitrous oxide container (16) further comprises a nitrous oxide container inlet (16B) positioned through the first housing middle opening (112MB). The nitrous oxide container inlet (16B) functions as a re-filling port. When a user bites on the rear mouthpiece (14R) nitrous oxide flows from the nitrous oxide container (16) through the mouthpiece (14) into the user's mouth and lungs.

13 Claims, 5 Drawing Sheets

NITROUS OXIDE DELIVERY SYSTEM

FIELD OF THE INVENTION

The present invention relates to gas delivery systems. More particularly, the present invention relates to oral gas delivery systems used as a substitute for smoking plant products and as an alternative analgesic, stress reducer, and pain reliever.

DESCRIPTION OF THE PRIOR ART

The recent war against smoking and the proven deadly tobacco use, as smoking decreases in acceptability a demand will be generated for a product to fill-in the expected void that will be created from regulating tobacco use and smoking. Assuming that the F.D.A will eventually regulate nicotine content in cigarettes and cigars to a non-addictive level, some smokers (addicted or non-addicted) would still choose to continue to smoke, to satisfy the developed habits of: "having something between their fingers, or in their hand, inhaling and exhaling to blow off the steam as a release of tension or stress reduction mechanism, and putting something between their lips—a persistence of a baby's nipple-suckling or a child's thumb-sucking, pleasurable reflex act.

Hence, it is expected that some smokers will not give up smoking even after nicotine regulation, to satisfy the above pleasurable habits, ignoring the real health-hazards derived from the tobacco "smoke" itself other than nicotine. The present invention meets the needs of those smokers with an alternative safe device. The present invention is a substance that can be inhaled from a device that fits between the fingers or in the hand (like a pipe) replacing cigarettes, cigars or pipes, and delivering an inhalant safe chemical. The present invention has attractive characteristics which replace tobacco use and to serve as a stress-reducing, recreational and non-addictive safe substitute.

The present invention uses nitrous oxide in low concentrations which is inhaled by the user. Nitrous oxide, in low concentrations, is "analgesic" in man. As little as 10% by volumes can produce a substantial effect and the inhalation of 20% of the gas in oxygen, has been shown to be as effective as 15 mgm of morphine sulfate (Chapman, et. Al., 1943). Its use to produce effective analgesia in the second stage of labor (even at higher concentrations) attests to its efficacy and safety, even to an unborn baby. Nitrous oxide is a colorless gas, without appreciable odor or taste. In the present invention nitrous oxide stored in a container under pressure and released through a valve. Since the vapor pressure at room temperature is approximately 50 atmospheres, as it is released from the cylinder, nitrous oxide returns to the gaseous state. The heat required for its vaporization is obtained from the walls of the cylinder and surrounding air, resulting in accumulation of a deposit of frost, that would require insulation of the container surface.

Further, nitrous oxide has the pharmacological effect of increased sympathetic nervous system activity. This effect is conceivably mild in smaller concentrations, and provides its user with an "adrenaline surge" or "rush", that would replace the nicotine stimulatory effect or the "high" derived from tobacco smoke. This effect produces the "laughing" effect, characteristic of the gas, and can presumably replace the recreational marijuana smoking and its analgesic usage in cancer and AIDS patients.

The preferred delivery system in the shape of a pipe or a cigar capable of accommodating a refillable steel container (a small cylinder or a bulb) insulated to protect against frost formation, with a push button gas-release system similar to an asthma inhaler, with a pressure-reducing mechanism to allow for a smooth puff to be inhaled.

As smoking in the United States decreases due to regulation, education and deaths associated with smoke related illnesses a substitute is need to satisfy the need of individuals who have given up smoking. There are at least three psychological needs that have been discovered related to smoking; need to have an article held in the hand, need is to have a an article held between the lips, and a need to release tension through the motion of exhaling and inhaling. Further, the nicotine high received from smoking will need to be replaced with a less toxic form. What is needed is a device that duplicates the tactile, pharma-psychological, and psychological satisfaction a user receives from a cigarette. One substitute for a cigarette that provides satisfies these need is a mixture of nitrous oxide and air.

The present invention functions as a substitute for tobacco or marijuana smoking, an analgesic, stress reducer, and pain reliever.

Numerous innovations for Nitrous Oxide Delivery System have been provided in the prior art that are described as follows. Even though these innovations may be suitable for the specific individual purposes to which they address, they differ from the present invention as hereinafter contrasted.

In U.S. Pat. No. 4,685,478, titled Thermophilic Denitrification of Tobacco, invented by Vedpal S. Malik, Bernard A. Semp, Hernan G. Bravo and Daniel M. Teng, high temperature processes and thermophilic organisms are used in processes for reducing the levels of certain nitrogen-containing compounds in tobacco materials. Tobacco materials are contacted with at least one thermophilic organism characterized by an anaerobic, dissimulator, metabolic pathway for denitrification of tobacco materials under anaerobic and high temperature conditions that promote such metabolism. Tobacco materials treated in accordance with these high temperature processes and thermophilic organisms, when incorporated into a smoking product, deliver a significantly reduced amount of oxide of nitrogen in smoke. Moreover, such tobacco materials also afford the product of other tobacco products having lower amounts of nitrates and other nitrogen-containing compounds.

The patented invention differs from the present invention because the patented invention is process for denitrification of tobacco. The present invention is a substitute for both tobacco and the smoking device. The present invention retains the tactile feel, physiological feel, and effects similar to a nicotine rush of current smoking products. The present invention is a cigarette substitute device comprising a container filled with $NO_2$ through a filling port. The $NO_2$ is stored in the container under pressure and released when the user activates a user actuated a gas release device such as a lip opened valve. The present invention can also have the form of an inhaler which releases the $NO_2$ into the user's mouth as the user inhales.

In Patent number D304,771, titled Pipe, invented by Yutaka Katayama, the ornamental design for a pipe, is as shown and described.

The patented invention differs from the present invention because the patented invention is an ornamental design for a pipe which lacks the features of a container, user actuated gas release device, and container filling port of present invention.

In Patent number D315,032, titled Pipe, invented by Kiel R Hayes, the ornamental design for a pipe, is as shown and described.

The patented invention differs from the present invention because the patented invention is an ornamental design for a pipe which lacks the features of a container, user actuated gas release device, and container filling port of present invention.

In Patent number D371,632, titled Smoking Pipe, invented by Michael T. Truelove, the ornamental design for a smoking pipe, is as shown.

The patented invention differs from the present invention because the patented invention is an ornamental design for a pipe which lacks the features of a container, user actuated gas release device, and container filling port of present invention.

In Patent number D371,633, titled Smoking Pipe, invented by Paul E. Chenard, the ornamental design for a smoking pipe, is as shown and described.

The patented invention differs from the present invention because the patented invention is an ornamental design for a pipe which lacks the features of a container, user actuated gas release device, and container filling port of the present invention.

In U.S. Pat. No. 4,549,563, titled Gas Mixers, invented by Jean-Pierre Monnier, a mixer for delivering a mixture of two gases G1 and G2 in proportions respectively and by volume of X/100 and (100-X)/100; x/100 not being allowed to be smaller than a particular value is described. Each gas circuit comprises a pipe provided with a cock for adjustment of the rate of flow and with a calibrated orifice selected in such manner that for an identical pressure P, the rates of flow of the gases through these orifices are int he ratio X/(100-X), with devices for limiting the pressure of the gas G2 to that of the gas G1, as well as for limiting the pressure in both circuits. The invention is applicable to an oxygen-nitrous oxide mixer for anaesthetic purposes, in which the proportion of oxygen in the mixture supplied cannot drop below 25% and the flow rate of nitrous oxide cannot exceed a predetermined maximum.

The patented invention differs from the present invention because the patented invention is a mixer for delivering a mixture of two gases. The present invention delivers a single gas which is mixed unregulated with atmospheric gasses as a user inhales.

Numerous innovations for Nitrous Oxide Delivery System have been provided in the prior art that are adapted to be used. Even though these innovations may be suitable for the specific individual purposes to which they address, they would not be suitable for the purposes of the present invention as heretofore described.

SUMMARY OF THE INVENTION

The present invention is a cigarette substitute device comprising a container filled with $NO_2$ through a filling port. The $NO_2$ is stored in the container under pressure and released when a user actuates a gas release device such as a lip opened valve. The present invention can also have the form of an inhaler which releases the $NO_2$ into the user's mouth as the user inhales.

The types of problems encountered in the prior art are mixing of concentrated gases with the atmosphere and delivering the combined mixture to an individual.

In the prior art, unsuccessful attempts to solve this problem were attempted namely gas regulation devices and delivery devices which require a operator and a mask to assure delivery of the desired concentration of gas. However, the problem was solved by the present invention because a small volume of concentrated gas is contained in a pressurized vessel having a user activated dispensing valve.

The present invention solved a long felt need for a cigarette substitute that satisfies the tactile, Pharm.-psychological, psychological satisfaction a user receives from a cigarette.

Accordingly, it is an object of the present invention to provide a cigarette substitute which delivers a substance that produces effects similar to nicotine without the toxic effects.

More particularly, it is an object of the present invention to provide a delivery system for dispensing nitrous oxide into a user respiratory system.

In keeping with these objects, and with others which will become apparent hereinafter, one feature of the present invention resides, briefly stated, in gas canister with a mouth actuated release device..

When the nitrous oxide delivery system is designed in accordance with the present invention, nitrous oxide gas is contained within a pressurized container and released under user control.

In accordance with another feature of the present invention, a mouthpiece is attached to a valve.

Another feature of the present invention is that the valve is actuated by the user placing the mouthpiece in the lips and closing the lips against a trigger which actuates the valve releasing the nitrous oxide gas.

Yet another feature of the present invention is that the container is filled with nitrous oxide through a nitrous oxide container inlet and the nitrous oxide gas is stored under pressure.

Still another feature of the present invention is that a mouth piece is adapted to fit a user's mouth.

Yet still another feature of the present invention is that the shape of the first nitrous oxide delivery system satisfies the tactile, pharma-phsycological, psychological needs of a user.

Still yet another feature of the present invention is that a housing is shaped like a cigar.

Another feature of the present invention is that a housing is shaped to resemble a pipe.

Yet another feature of the present invention is that a housing is shaped to resemble a cigarette.

The novel features which are considered characteristic for the invention are set forth in the appended claims. The invention itself, however, both as to its construction and its method of operation, together with additional objects and advantages thereof will be best understood from the following description of the specific embodiments when read and understood in connection with the accompanying drawings.

LIST OF REFERENCE NUMERALS UTILIZED
IN THE DRAWINGS
COMMON COMPONENTS TO EMBODIMENTS
14—mouthpiece (14)
14F—front mouthpiece (14F)
14R—rear mouthpiece (14R)
14A—mouthpiece ring (14A)
14B—mouthpiece ball (14B)
14C—mouthpiece bump (14C)
16—nitrous oxide container (16)
16A—nitrous oxide container outlet (16A)
16B—nitrous oxide container inlet (16B)
FIRST EMBODIMENT
110—first nitrous oxide delivery system (110)
112—first housing (112)
112—first housing fill (112A)
112F—first housing front (112F)
112R—first housing rear (112R)

112M—first housing middle (112M)
112MA—first housing middle chamber (112MA)
112MB—first housing middle opening (112MB)
SECOND EMBODIMENT
210—second nitrous oxide delivery system (210)
212—second housing (212)
212A—second housing fill (212A)
212B—second housing container housing (212B)
212BA—second housing container housing chamber (212BA)
212BB—second housing container housing opening (212BB)
212BC—second housing container housing lid (212BC)
212C—second housing stem (212C)

DESCRIPTION OF THE PREFERRED EMBODIMENT

Figure 1:
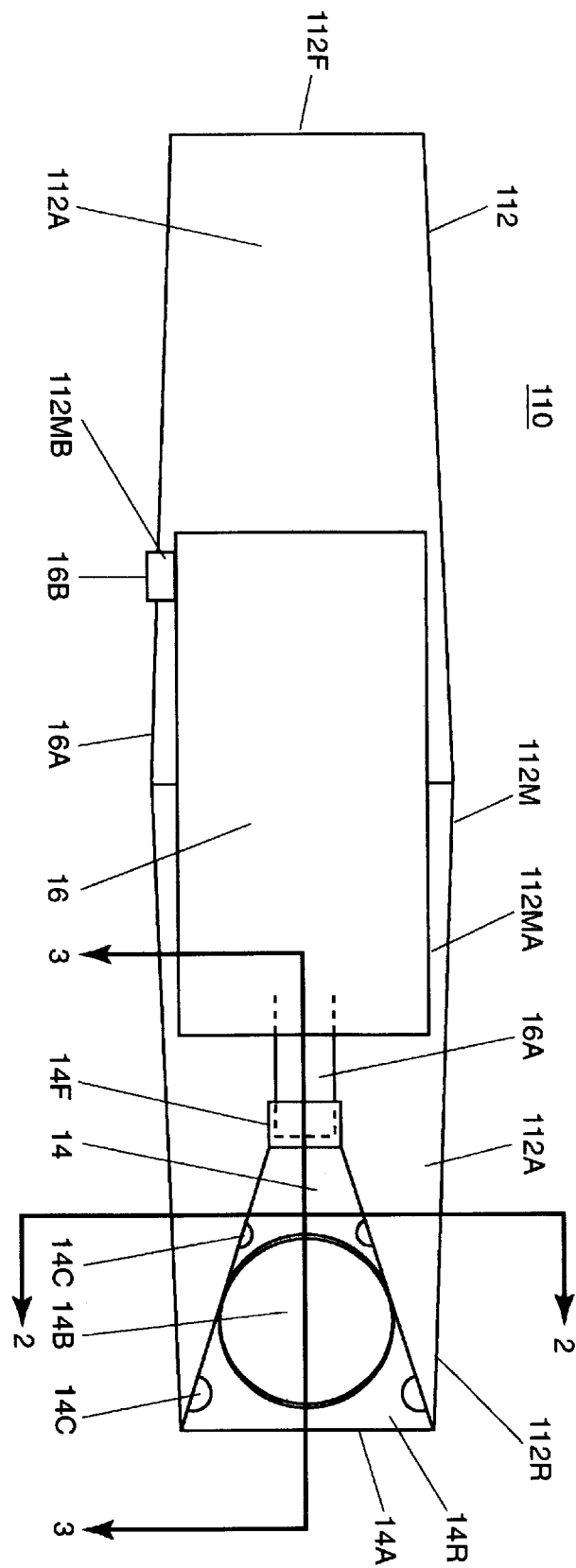
FIG. 1 is a side view of a first nitrous oxide delivery system.

Firstly, referring to FIG. 1 which is a side view of a first nitrous oxide delivery system (110) which comprises a first housing (112) containing first housing fill (112A). The first housing (112) comprises a first housing front (112F), a first housing rear (112R), a first housing middle (112M) having a first housing middle chamber (112MA) therein and a first housing middle opening (112MB) therethrough. The first housing (112) is configured in a shape of a cigar. The first housing fill (112A) is insulation functioning to prevent frosting when the nitrous oxide is released from the nitrous oxide container (16). The first housing (112) is manufactured from a material selected from a group consisting of metal, metal alloy, plastic, plastic composite, epoxy, fiberglass, carbon-graphite, rubber. And rubber composite. The first housing front (112F) is removable from the first housing rear (112R) functioning to allow access to the first housing middle chamber (112MA) to replace the nitrous oxide container (16) therein.

The first nitrous oxide delivery system (110) further comprises a mouthpiece (14) is positioned within the first housing front (112F). The mouthpiece (14) comprises a front mouthpiece (14F) and a rear mouthpiece (14R). A mouthpiece ring (14A) is sealably mounted at a distal end of the rear mouthpiece (14R). The mouthpiece (14) is manufactured from a material selected from a group consisting of metal, metal alloy, plastic, plastic composite, epoxy, fiberglass, carbon-graphite, rubber, and rubber composite. A mouthpiece ball (14B) is movably mounted within the rear mouthpiece (14R) in front of the mouthpiece ring (14A). At least one mouthpiece bump (14C) is securely mounted within the rear mouthpiece (14R) extending inwardly thereof in front of the mouthpiece ball (14B). The mouthpiece ring (14A) comprises a complimentary configuration to the mouthpiece ball (14B) functioning to form a seal therebetween when the first nitrous oxide delivery system (110) is not used.

The first nitrous oxide delivery system (110) further comprises a nitrous oxide container (16) positioned within the first housing middle chamber (112MA). The nitrous oxide container (16) comprises a nitrous oxide container outlet (16A) sealaby attached to the front mouthpiece (14F). The nitrous oxide container (16) further comprises a nitrous oxide container inlet (16B) positioned through the first housing middle opening (112MB). The nitrous oxide container inlet (16B) functions as a re-filling port. When a user bites on the rear mouthpiece (14R), the mouthpiece ball (14B) moves in a frontwards direction away from the mouthpiece ring (14A) allowing nitrous oxide to flow from the nitrous oxide container (16) through the mouthpiece (14) into the user's mouth and lungs.

Figure 2:
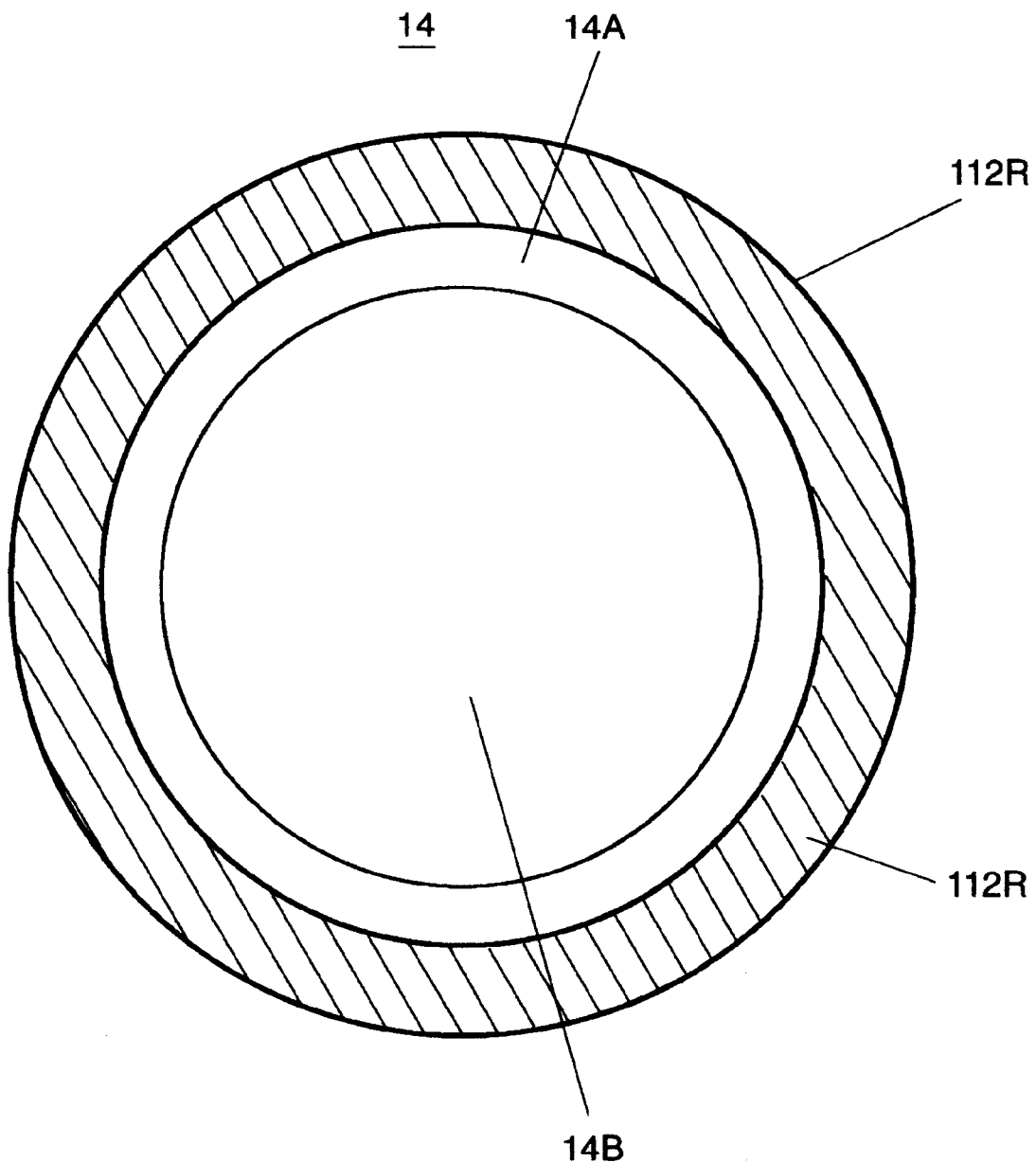
FIG. 2 is a cross sectional view of a first housing rear.

Secondly, referring to FIG. 2 which is a cross sectional view of a first housing rear (112R) which comprises mouthpiece (14) which is positioned within the first housing rear (112R). A mouthpiece ring (14A) comprises a complimentary configuration to the mouthpiece ball (14B) functioning to form a seal therebetween.

Figure 3:
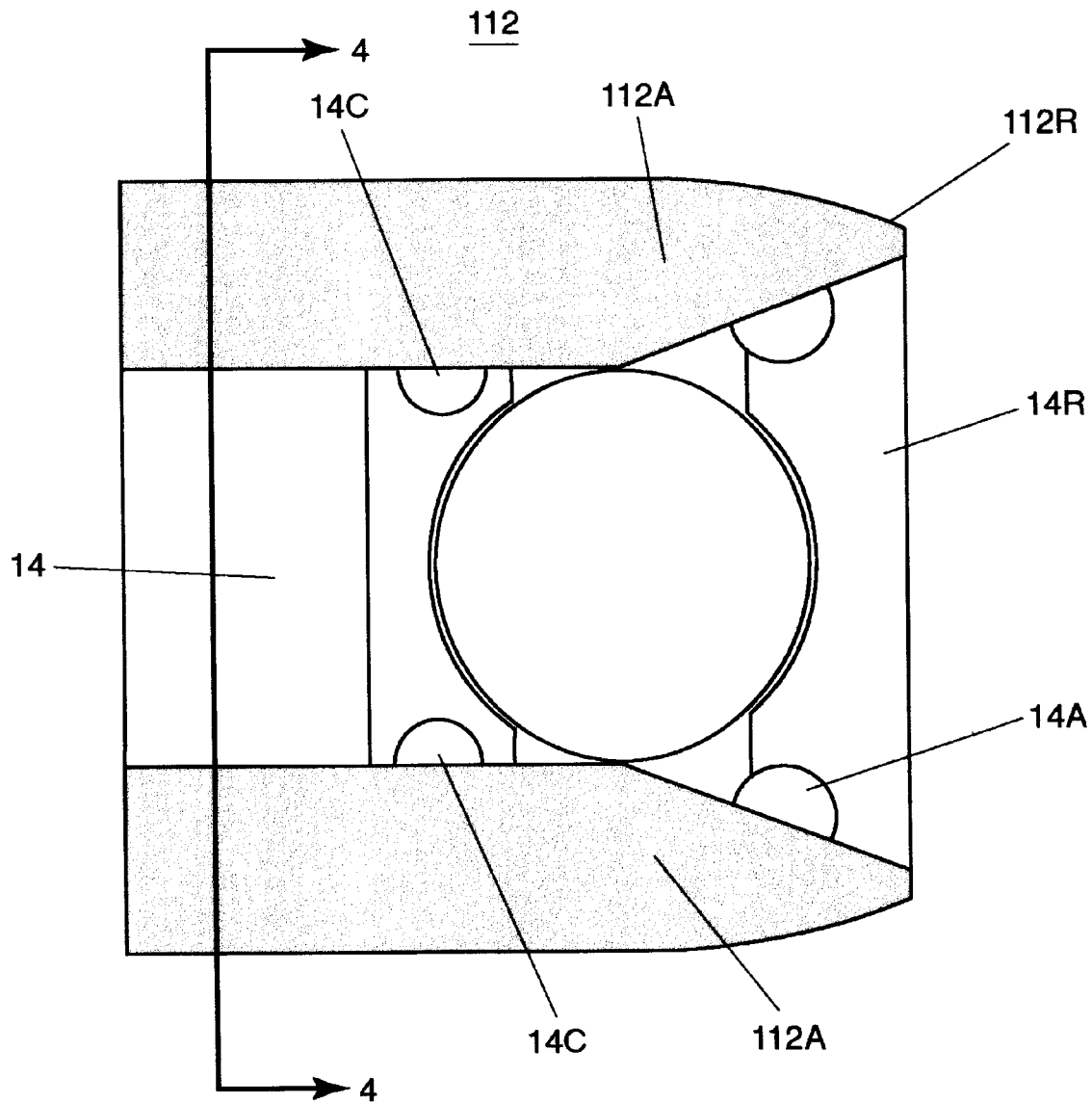
FIG. 3 is a cross sectional view of a first housing.

Thirdly, referring to FIG. 3 which is a cross sectional view of a first housing (112). The first housing (112) comprises a first housing fill (112A). The first housing (112) is configured in a shape of a cigar. The first housing fill (112A) is insulation functioning to prevent frosting when the nitrous oxide is.

Figure 4:
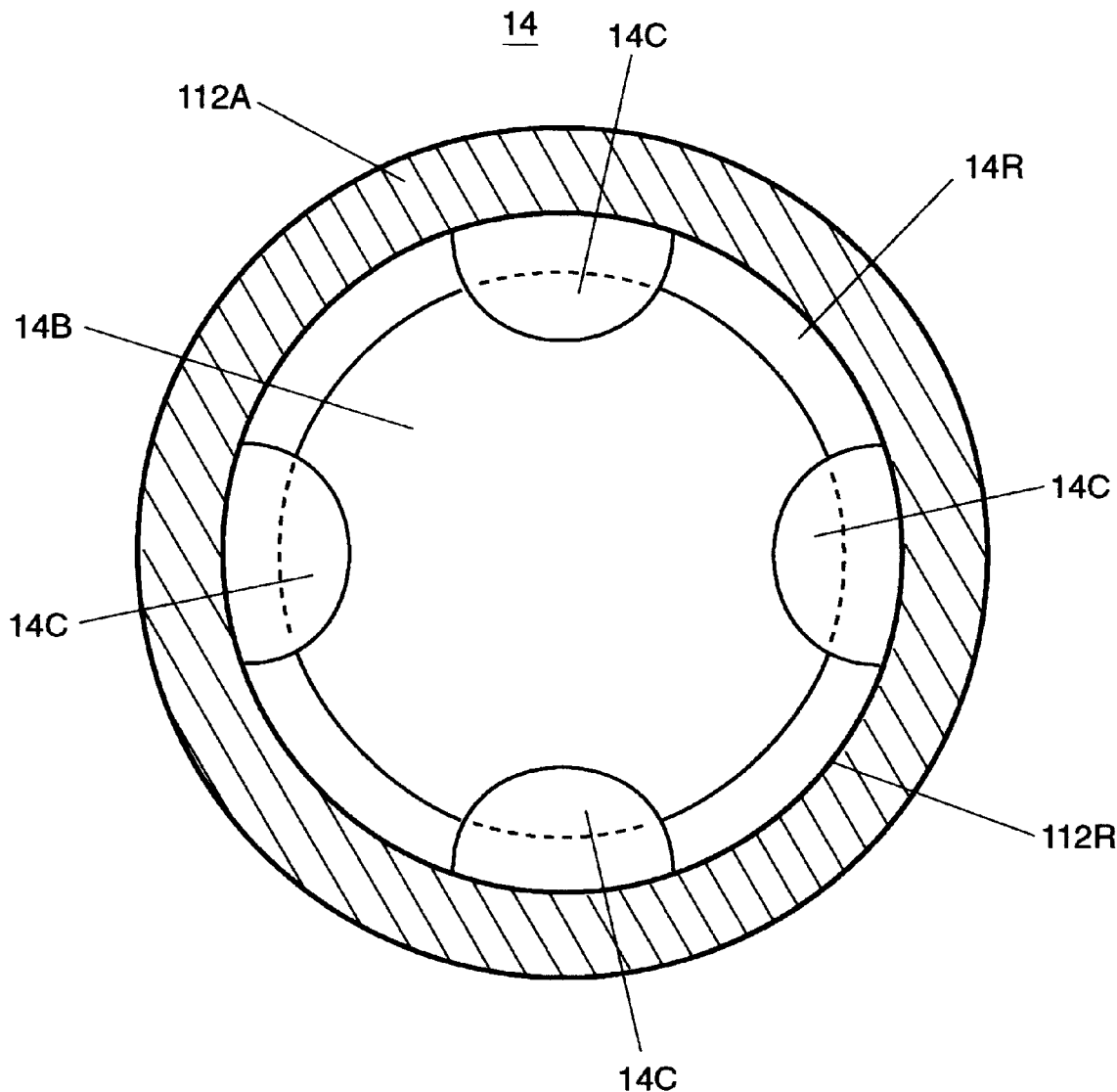
FIG. 4 is a cross sectional view of a mouthpiece.

Now, referring to FIG. 4 which is a cross sectional view of a mouthpiece (14). The mouthpiece (14) comprises a mouthpiece ball (14B) is movably mounted within the rear mouthpiece (14R). At least one mouthpiece bump (14C) is securely mounted within the rear mouthpiece (14R) extending inwardly thereof in front of the mouthpiece ball (14B).

Figure 5:
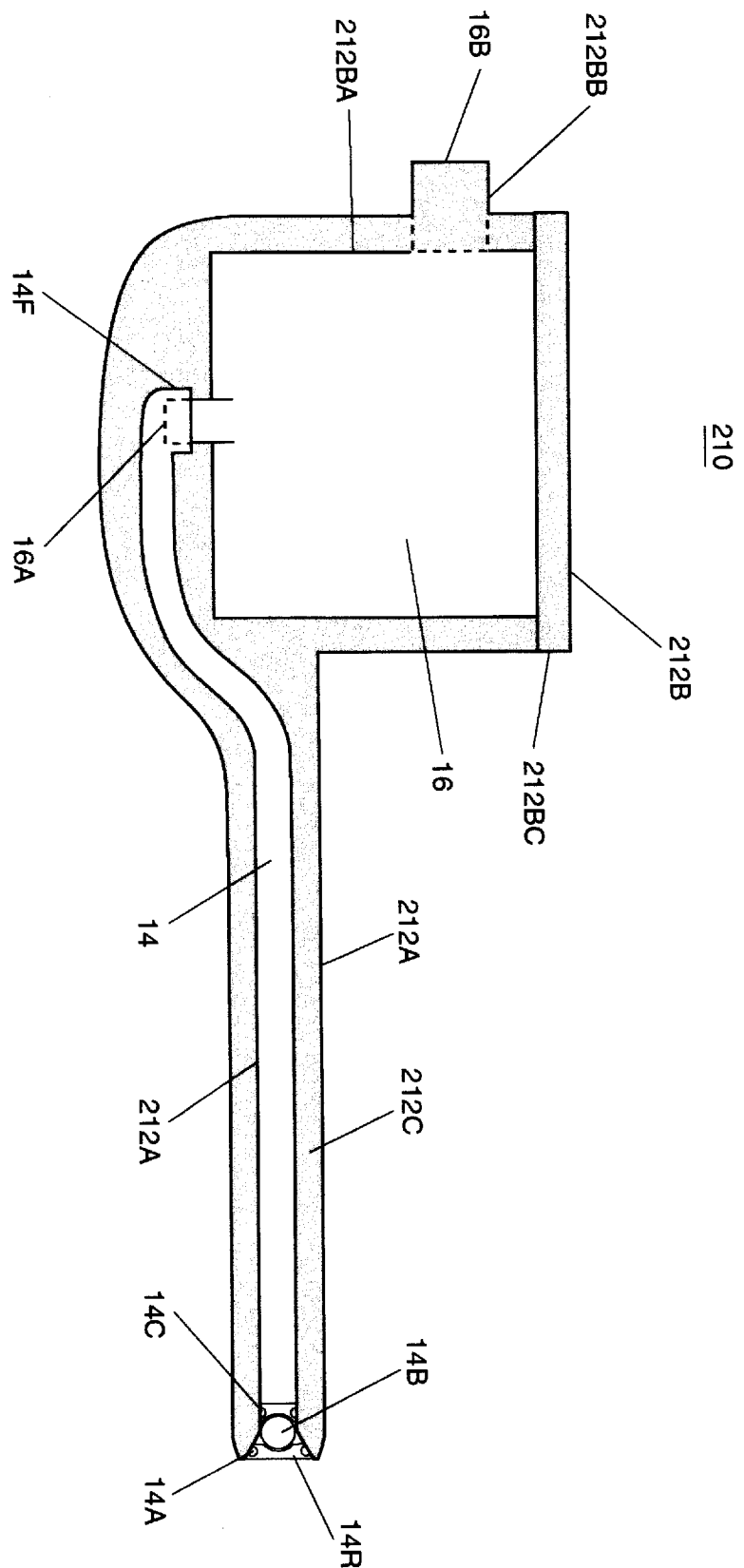
FIG. 5 is a cross sectional view of a second nitrous oxide delivery system.

Lastly, referring to FIG. 5 which is a cross sectional view of a second nitrous oxide delivery system (210). The second nitrous oxide delivery system (210) comprises a mouthpiece (14) which is positioned within the second housing container housing (212B). The mouthpiece (14) comprises a front mouthpiece (14F) and a rear mouthpiece (14R). A mouthpiece ring (14A) is sealably mounted at a distal end of the rear mouthpiece (14R). A mouthpiece ball (14B) is movably mounted within the rear mouthpiece (14R) in front of the mouthpiece ring (14A). At least one mouthpiece bump (14C) is securely mounted within the rear mouthpiece (14R) extending inwardly thereof in front of the mouthpiece ball (14B). The mouthpiece ring (14A) comprises a complimentary configuration to the mouthpiece ball (14B) functioning to form a seal therebetween when the second nitrous oxide delivery system (210) is not used.

The mouthpiece (14) is manufactured from a material selected from a group consisting of metal metal alloy, plastic, plastic composite, epoxy, fiberglass, carbon-graphite, rubber. And rubber composite.

A second nitrous oxide delivery system (210) further comprises a nitrous oxide container (16) positioned within the second housing container housing chamber (212BA). The nitrous oxide container (16) comprises a nitrous oxide container outlet (16A) sealaby attached to the front mouthpiece (14F). The nitrous oxide container (16) further comprises a nitrous oxide container inlet (16B) positioned through the second housing container housing opening (212BB). The nitrous oxide container inlet (166B) functions as a re-filling port. When a user bites on the rear mouthpiece (14R), the mouthpiece ball (14B) moves in a frontwards direction away from the mouthpiece ring (14A) allowing nitrous oxide to flow from the nitrous oxide container (16) through the mouthpiece (14) into the user's mouth and lungs.

It will be understood that each of the elements described above, or two or more together, may also find a useful application in other types of constructions differing from the type described above.

While the invention has been illustrated and described as embodied in a Nitrous Oxide Delivery System, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by letters patent is set forth in the appended claims.

What is claimed is:

1. A first nitrous oxide delivery system (110) comprising:
   A) a first housing (112) containing first housing fill (112A), the first housing (112) comprises a first housing front (112F), a first housing rear (112R), a first housing middle (112M) having a first housing middle chamber (112MA) therein and a first housing middle opening (112MB) therethrough, the first housing (112) is configured in a shape of a cigar;
   B) a mouthpiece (14) is positioned within the first housing front (112F), the mouthpiece (14) comprises a front mouthpiece (14F) and a rear mouthpiece (14R), a mouthpiece ring (14A) is sealably mounted at a distal end of the rear mouthpiece (14R), a mouthpiece ball (14B) is movably mounted within the rear mouthpiece (14R) in front of the mouthpiece ring (14A), at least one mouthpiece bump (14C) is securely mounted within the rear mouthpiece (14R) extending inwardly thereof in front of the mouthpiece ball (14B), the mouthpiece ring (14A) comprises a complimentary configuration to the mouthpiece ball (14B) functioning to form a seal therebetween when the first nitrous oxide delivery system (110) is not used; and
   C) a nitrous oxide container (16) positioned within the first housing middle chamber (112MA), the nitrous oxide container (16) comprises a nitrous oxide container outlet (16A) sealaby attached to the front mouthpiece (14F), the nitrous oxide container (16) further comprises a nitrous oxide container inlet (16B) positioned through the first housing middle opening (112MB), the nitrous oxide container inlet (16B) functions as a re-filling port, when a user bites on the rear mouthpiece (14R), the mouthpiece ball (14B) moves in a frontwards direction away from the mouthpiece ring (14A) allowing nitrous oxide to flow from the nitrous oxide container (16) through the mouthpiece (14) into the user's mouth and lungs.

2. The first nitrous oxide delivery system (110) as described in claim 1, wherein the first housing fill (112A) is insulation functioning to prevent frosting when the nitrous oxide is released from the nitrous oxide container (16).

3. The first nitrous oxide delivery system (110) as described in claim 1, wherein the mouthpiece (14) is manufactured from a material selected from a group consisting of metal, metal alloy, plastic, plastic composite, epoxy, fiberglass, carbon-graphite, rubber, and rubber composite.

4. The first nitrous oxide delivery system (110) as described in claim 1, wherein the first housing (112) is manufactured from a material selected from a group consisting of metal, metal alloy, plastic, plastic composite, epoxy, fiberglass, carbon-graphite, rubber, and rubber composite.

5. The first nitrous oxide delivery system (110) as described in claim 1, wherein the first housing front (112F) is removable from the first housing rear (112R) functioning to allow access to the first housing middle chamber (112MA) to replace the nitrous oxide container (116) therein.

6. A second nitrous oxide delivery system (210) comprising:
   A) a second housing (212) containing second housing fill (212A), the second housing (212) comprises a second housing container housing (212B) securely fastened at a substantially perpendicular angle to a second housing stem (212C) extending therefrom, the second housing container housing (212B) comprises a second housing container housing chamber (212BA) therein and a second housing container housing opening (212BB) therethrough;
   B) a mouthpiece (14) is positioned within the second housing container housing (212B), the mouthpiece (14) comprises a front mouthpiece (14F) and a rear mouthpiece (14R), a mouthpiece ring (14A) is sealably mounted at a distal end of the rear mouthpiece (14R), a mouthpiece ball (14B) is movably mounted within the rear mouthpiece (14R) in front of the mouthpiece ring (14A), at least one mouthpiece bump (14C) is securely mounted within the rear mouthpiece (14R) extending inwardly thereof in front of the mouthpiece ball (14B), the mouthpiece ring (14A) comprises a complimentary configuration to the mouthpiece ball (14B) functioning to form a seal therebetween when the second nitrous oxide delivery system (210) is not used; and
   C) a nitrous oxide container (16) positioned within the second housing container housing chamber (212BA), the nitrous oxide container (16) comprises a nitrous oxide container outlet (16A) sealaby attached to the front mouthpiece (14F), the nitrous oxide container (16) further comprises a nitrous oxide container inlet (16B) positioned through the second housing container housing opening (212BB), the nitrous oxide container inlet (16B) functions as a re-filling port, when a user bites on the rear mouthpiece (14R), the mouthpiece ball (14B) moves in a frontwards direction away from the mouthpiece ring (14A) allowing nitrous oxide to flow from the nitrous oxide container (16) through the mouthpiece (14) into a user's mouth and lungs.

7. The second nitrous oxide delivery system (210) as described in claim 6, wherein the second housing fill (212A) is insulation functioning to prevent frosting when the nitrous oxide is released from the nitrous oxide container (16).

8. The second nitrous oxide delivery system (210) as described in claim 6, wherein the mouthpiece (14) is manufactured from a material selected from a group consisting of metal, metal alloy, plastic, plastic composite, epoxy, fiberglass, carbon-graphite, rubber, and rubber composite.

9. The second nitrous oxide delivery system (210) as described in claim 6, wherein the second housing (212) is manufactured from a material selected from a group consisting of metal, metal alloy, plastic, plastic composite, epoxy, fiberglass, carbon-graphite, rubber, and rubber composite.

10. The second nitrous oxide delivery system (210) as described in claim 6, wherein the second housing container housing (212B) further comprises a second housing container housing lid (212BC) removably positioned thereover, the functioning to allow access to the second housing container housing chamber (212BA) to replace the nitrous oxide container (16) therein.

11. The second nitrous oxide delivery system (210) as described in claim 6, wherein the second housing container housing (212B) is configured in a shape of a pipe bowl.

12. The second nitrous oxide delivery system (210) as described in claim 11, wherein the second housing stem (212C) is configured in a shape of a pipe mouthpiece.

13. The second nitrous oxide delivery system (210) as described in claim 6, wherein the second housing stem (212C) is configured in a shape of a cigarette.

* * * * *

UNITED STATES PATENT AND TRADEMARK OFFICE
CERTIFICATE OF CORRECTION

PATENT NO. : 6,016,801
DATED : January 25, 2000
INVENTOR(S) : Monir W. Phillips

It is certified that error appears in the above-identified patent and that said Letters Patent is hereby corrected as shown below:

<u>Title page, Item [54] and Column 1, line 1,</u>
Title, should read -- HAND-HELD NITROUS OXIDE DELIVERY SYSTEM --.

Signed and Sealed this

Twenty-fourth Day of December, 2002

JAMES E. ROGAN
*Director of the United States Patent and Trademark Office*